(12) United States Patent
Irland

(10) Patent No.: US 7,854,237 B2
(45) Date of Patent: Dec. 21, 2010

(54) FETAL MONITORING TRANSDUCER ALIGNING DEVICE

(76) Inventor: Nancy Beck Irland, 6375 NW. 268th Pl., Hillsboro, OR (US) 97124

( * ) Notice: Subject to any disclaimer, the term of this patent is extended or adjusted under 35 U.S.C. 154(b) by 791 days.

(21) Appl. No.: 11/770,025

(22) Filed: Jun. 28, 2007

(65) Prior Publication Data

US 2009/0005690 A1    Jan. 1, 2009

(51) Int. Cl.
*F16K 15/20* (2006.01)
(52) U.S. Cl. .................. 137/223; 600/490; 600/492; 600/498
(58) Field of Classification Search .......... 137/223, 137/225, 228; 600/490, 492, 498, 499, 202, 600/338, 313, 344, 376, 472
See application file for complete search history.

(56) References Cited

U.S. PATENT DOCUMENTS

| | | | | |
|---|---|---|---|---|
| 1,881,655 | A * | 10/1932 | Katz | 137/223 |
| 2,223,007 | A * | 11/1940 | Legowsky et al. | 137/223 |
| 2,694,395 | A | 5/1954 | Brown | |
| 3,379,901 | A * | 4/1968 | Richards | 600/459 |
| 3,780,725 | A * | 12/1973 | Goldberg | 600/453 |
| 3,859,984 | A * | 1/1975 | Langley | 600/453 |
| 4,570,691 | A * | 2/1986 | Martus | 137/223 |
| 4,640,295 | A * | 2/1987 | Isaacson | 600/588 |
| 4,781,200 | A | 11/1988 | Baker | |
| 4,920,966 | A | 5/1990 | Hon et al. | |
| 4,974,593 | A * | 12/1990 | Ng | 600/587 |
| 4,987,898 | A * | 1/1991 | Sones | 600/398 |
| 5,288,286 | A | 2/1994 | Davis et al. | |
| 5,373,843 | A | 12/1994 | Quedens et al. | |
| 5,931,797 | A | 8/1999 | Tumey et al. | |
| 6,048,323 | A * | 4/2000 | Hon | 600/588 |
| 6,134,460 | A * | 10/2000 | Chance | 600/344 |
| 6,151,520 | A | 11/2000 | Combs | |
| 6,749,573 | B2 * | 6/2004 | Bryant et al. | 600/528 |
| 6,781,569 | B1 | 8/2004 | Gregorio et al. | |
| 7,016,716 | B2 | 3/2006 | Rall et al. | |
| 7,063,676 | B2 | 6/2006 | Barak et al. | |
| 7,284,730 | B2 * | 10/2007 | Walsh et al. | 248/74.3 |

* cited by examiner

*Primary Examiner*—John Rivell
*Assistant Examiner*—Craig Price
(74) *Attorney, Agent, or Firm*—Peter A. Haas Esquire LLC

(57) ABSTRACT

To better position an ultrasonic transducer typically used in non-invasive fetal monitoring during labor, the present invention consists of a transducer-aligning device having a plurality of selectively fillable chambers, each chamber having a resiliently deformable side-wall. A fluid, such as air, can be selectively pumped or released into any combination of the chambers. When coupled to an ultrasonic transducer, the selective use of air pressure in the bladder more precisely aligns and positions the fetal monitor transducer to improve imaging. In a second embodiment, the present invention includes a solid wedge-shaped protrusion extending below the bottom surface of the housing and adapted to rotate about 360-degrees to enable a care-giver to selectively position the wedge and thus align the associated transducer for optimal readings of fetal heart rate.

11 Claims, 9 Drawing Sheets

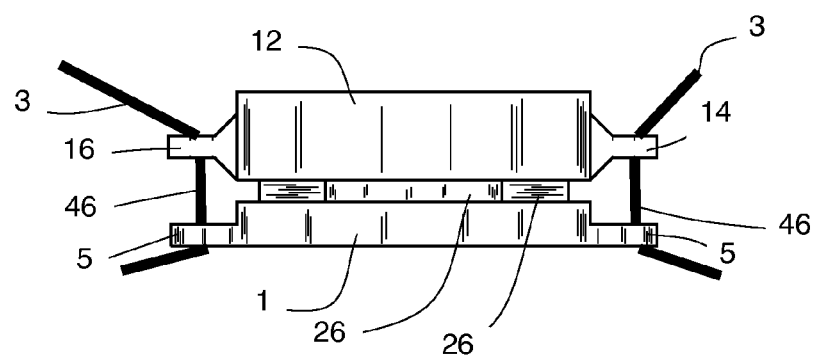
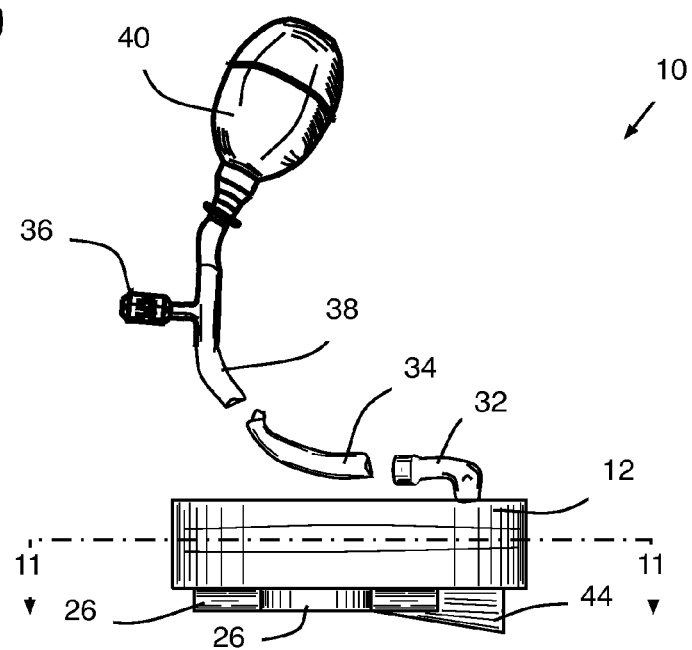

FETAL MONITORING TRANSDUCER ALIGNING DEVICE

BACKGROUND

This invention relates to fetal monitoring devices and more specifically to an improved interface apparatus adapted to better position electronic transducers on women during labor.

Practitioners and hospitals routinely use continual or periodic fetal monitoring during labor. Fetal monitoring is also performed on the patient during some prenatal consultations. This enables the practitioner to assess the condition of the fetus during antepartum, labor and delivery.

Electronic fetal monitoring (EFM), a preferred technique of fetal monitoring, uses an electronic monitoring and recording machine to process signals transmitted from sensors or transducers positioned on the patient. For example, during labor, the EFM system continuously monitors and records the fetal heart rate (FHR) and uterine contractions. The transducers connect either by wireless telemetry or by a hard-wired cable directly to the recording and monitoring machine. Examples of fetal monitoring machines include, but are not limited to, the system described in U.S. Pat. No. 4,781,200 to Baker issued on 01 Nov. 1988. Another example of a fetal monitoring machine is brand Corometrics 250-series model number 0172WAT-B manufactured by GE Healthcare Technologies of Waukesha, Wis. USA. Other machines made by Hewlett-Packard, for example, are also contemplated.

Electronic fetal monitor devices automatically and continuously monitor and record the heart rate of the fetus to assist practitioners in assessing the well-being and status of the fetus. Electronic fetal monitors include one or more fetal cardiac sensors including acoustic, electro-cardiographic, or bioimpedence type sensors. The electronic fetal monitor device converts sensor signals into digital signals for processing and recording. Recording includes printing a time-based paper record of the parameters measured along with a computer-generated reading stored on a disk and hard drive.

Non-invasive, external fetal monitoring techniques are most commonly employed during labor and delivery. This non-invasive technique incorporates ultrasonic waves to reflect off the fetal heart and are sensed by an appropriate sensor and process to determine the frequency shift associated with the reflection from the moving fetal heart valve according to the Doppler Principle.

This ultra-sonic, non-invasive technique crucially relies on the proper placement Including location and direction or angle of the external sensor or transducers on the patient. The two disk-like electronic transducers position on the patient's abdomen and are held in place by wider, stretch bands that circle the entire torso. The stretch bands, also termed a sensor belt, include one or more pieces of flexible, expandable material adapted to accommodate the curves of the maternal midsection during the later stages of pregnancy. Typically, the belt pieces adapt to extend over portions of the patient's abdomen and are made from a stretchable material, such as the type sold under the trade name Lycra or Spandex. A type of hook-and-loop closure, such as Velcro-brand fastener, enables opposing ends of the belt to releasably and selectively couple together. And, the belt feeds through two opposing slots arranged on either side of the transducer. An example of an ultrasound transducer holder is described in U.S. Pat. No. 4,920,966 to Hon et al. issued on 1 May, 1990.

To obtain accurate readings of both the FHR and uterine contractions, each respective transducer must be appropriately aligned and positioned on the patient's abdomen. This alignment requires practiced skill because to record the FHR, not only must the transducer be properly located on the abdomen of the patient, it must be simultaneously directed toward the heart valve of the fetus. Additionally, the strap or belt members used to retain the transducer must be both snug enough to maintain proper alignment of the transducer, yet be comfortable to the laboring patient.

A misalignment of the transducer will prevent accurate readings, send false readings, or not register readings. Once properly placed the transducer is continually exposed to erratic movements of the patient and position changes, movements, and descent of the fetus. And, even moderate movement of the patient or fetus can result in erroneous readings.

To maintain useful readings from the transducers, the practitioner must frequently re-position the transducer. This often requires considerable effort by the practitioner. Sometimes, the practitioner must manually hold the transducer in place to record the FHR for a period of time. Alternatively, in some instances the patient must remain in one position for a set period of time to allow a recording of the FHR. These approaches are often not feasible and the only alternative is to utilize an invasive form of fetal monitoring. One common invasive technique teaches placing an electrode on the fetal scalp. When a fetal scalp electrode is contra-indicated due to the patient's medical condition or fetal presentation, and the practitioner cannot remain at the patient's bedside to manually hold the transducer in the exact position, the patient may be required to stay in one position throughout the labor to facilitate adequate monitoring of the fetus; however, labor dystocia can occur, thus necessitating a cesarean section.

Therefore, there is a need for an improved fetal monitoring transducer mounting system and apparatus that enables a practitioner to more precisely change and maintain the angle of an ultrasonic transducer. Further, such a system and apparatus should readily adapt to existing transducers already being used by practitioners in clinics and hospital delivery rooms.

DRAWING

FIG. 8 is a side view of an alternative embodiment of the present invention and shows one possible coupling arrangement of the device to a transducer of the prior art.

FIG. 10 is a side view of one system according to the present invention including a transducer aligning device and pump apparatus and showing one inflatable membrane extended.

DESCRIPTION OF THE INVENTION

Figure 1:
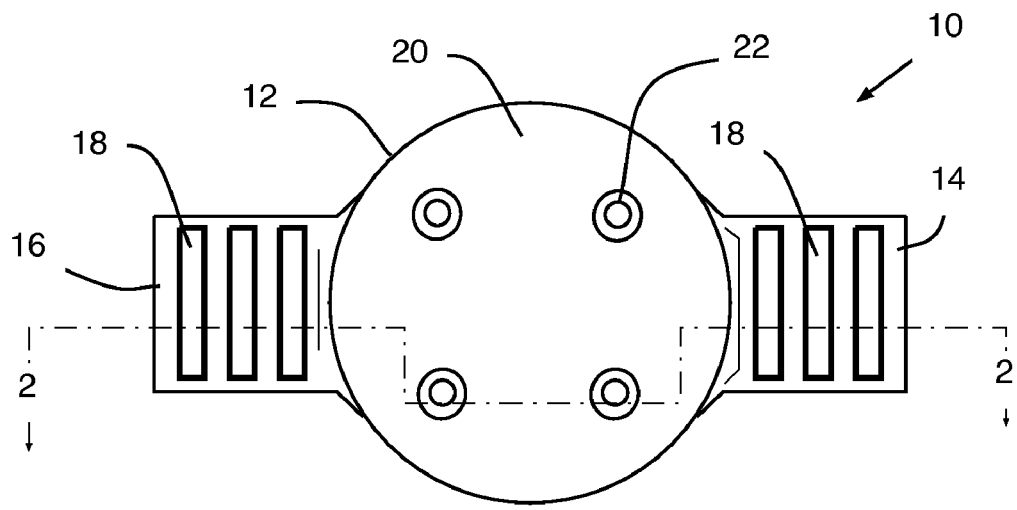
FIG. 1 is a top view of a device according to the present invention.

The present invention, described herein and illustrated in the accompanying figures of the drawing, is portrayed through the use of exemplary embodiments that represent its spirit and scope. Further, in the various figures certain components may be omitted or exaggerated to more clearly illustrate a particular aspect of the invention. And, those skilled in the art will appreciate that various combinations of elements, substitutions of elements, omissions and deletions of elements will not deviate from the spirit and intent of the present invention. The scope of the invention shall be limited only by the appropriate construction of the claims that follow.

The various embodiments of the fetal monitor transducer aligning device of the present invention adapt to work in conjunction with all known fetal monitoring transducers. The prior art is replete with examples of such compatible transducers. By no means an exhaustive list, the following represent the variety of transducers understood in the art. Such transducers include the hard-wired type as described by Quedens et al. in U.S. Pat. No. 5,373,843 issued on 20 Dec. 1994 or the type described by Combs in U.S. Pat. No. 6,151,520 issued on 21 Nov. 2000. Other types of transducers include such devices as described by Hon et al. in U.S. Pat. No. 4,920,966 issued on 01 May 1990. All these aforementioned references are included by reference as if fully set forth herein. Accordingly, it will be appreciated by those skilled in the art that various configurations of the present invention may be tailored to better suit a particular transducer.

A common problem with prior art transducers is the ability to precisely align the transducer on the patient's abdomen to maximize the desired readings, whether such readings include the fetal heart rate, or uterine contractions. The transducer is typically placed with a sound-coupling enhancing jelly on the patient's abdomen and retained in position by a transducer belt or stretch bands that encircle the patient's torso. Should the care provider wish to re-position the transducer, even slightly adjust its location, great effort of re-positioning the encircling bands must be undertaken on a patient that is likely in discomfort during the pains of labor. Additionally, the existing prior-art devices and teachings do not provide any means for adjusting and maintaining the pitch and rake of the transducer to follow the movements of the fetus as it proceeds through the pelvis in a rotating manner during labor. The transducer is simply placed tangentially or parallel with the particular location on the abdomen.

The present invention, however, includes means for easily and quickly adjusting the attitude of the transducer, particularly with respect to the rake and pitch of the transducer relative to the surface of the abdomen.

Figure 2:
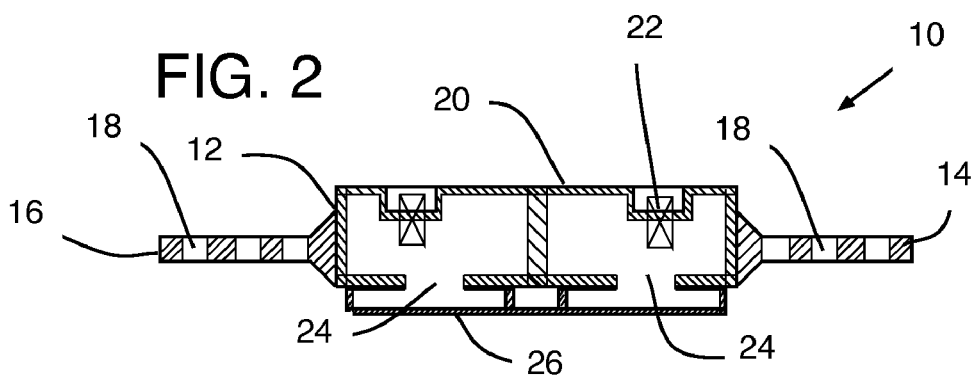
FIG. 2 is a cross-section showing the profile of the device of FIG. 1 along the line 2-2 of FIG. 1.
Figure 3:
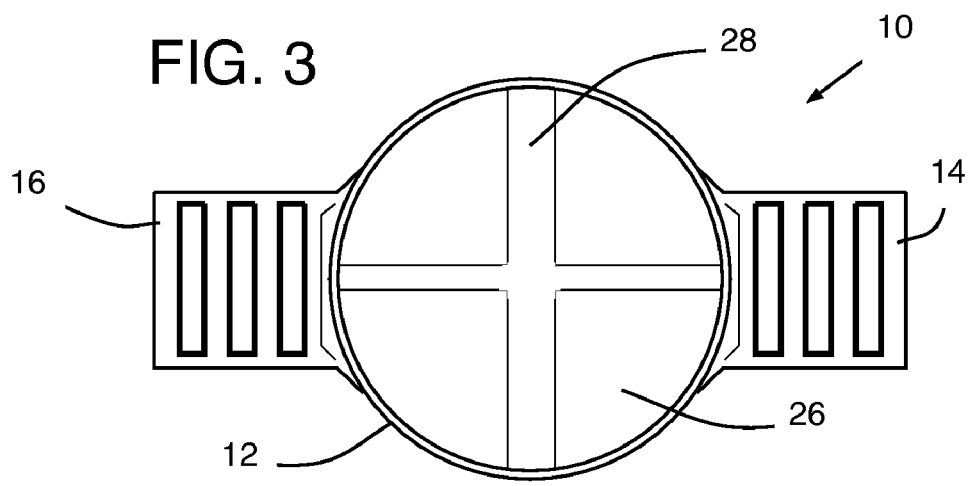
FIG. 3 is a bottom view of the device of FIG. 1.

FIGS. 1-13 illustrate various embodiments of the present invention. In one embodiment, as FIGS. 1, 2 and 3 show, an aligning device 10 for a fetal monitoring transducer includes a disk shaped cylindrical body housing 12 having a base 28 and top 20. One possible material for the housing includes an injection-molded plastic as would be well understood in the medical device industry.

Figure 13:
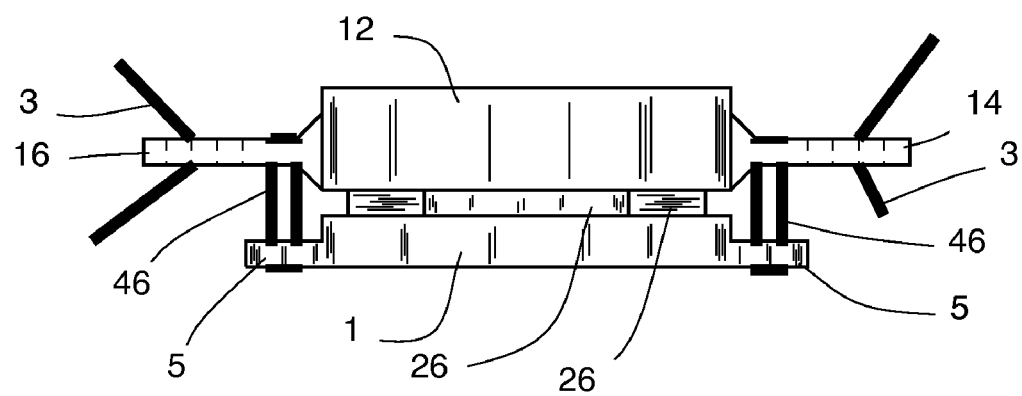
FIG. 13 is a side view showing a device according to one embodiment of the present invention coupled to a transducer of the prior art.
Figure 14:
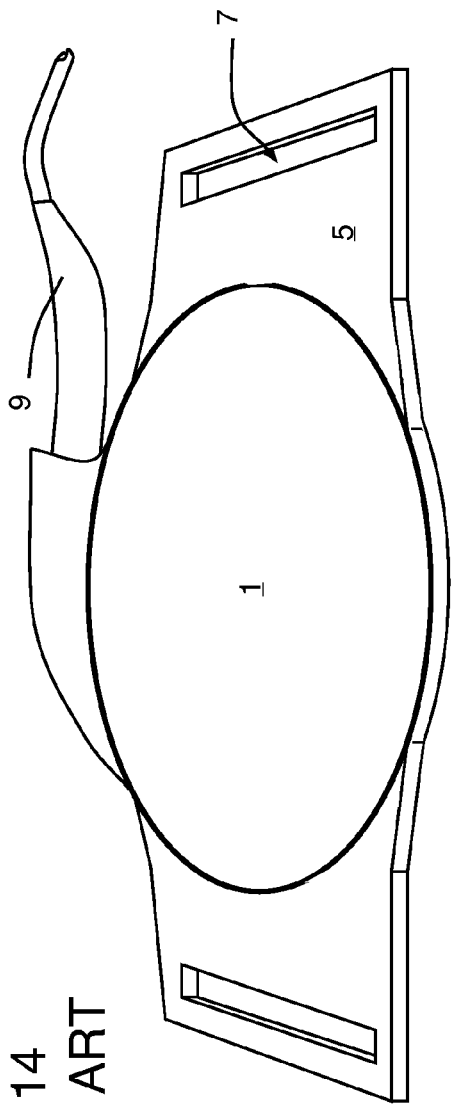
FIG. 14 is an offset top view of a possible fetal monitor transducer according to the teachings of the prior art.
Figure 15:
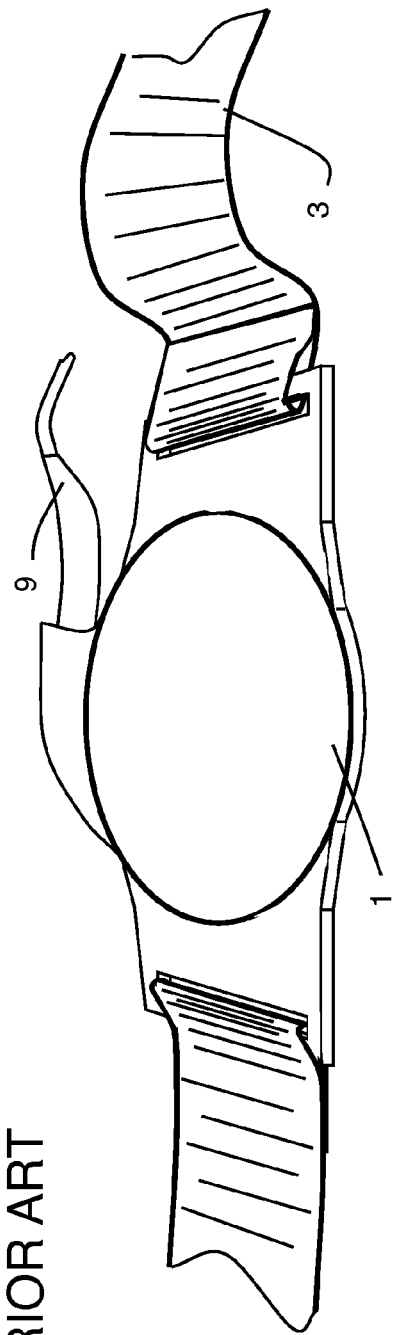
FIG. 15 is an offset top view of a possible fetal monitor transducer according to the teachings of the prior art and includes a belt or stretch bands as taught by the prior art.

The housing body is flanked by two, oppositely disposed arms 14 and 16. Each arm includes one or more slots 18, which adapt to receive a stretch band, also called a transducer belt 3 as is commonly understood in the art. For example, A pair of arms protrudes from the housing body 12. A first arm 14 is disposed opposite from the second arm 16 with the housing body disposed intermediate to the each arm. The first arm includes one or more slots 18, each slot is adapted to receive a coupling means. Similarly, the second arm includes a second plurality of slots adapted to receive a second coupling means. One suitable coupling means includes a transducer belt of the prior art. Another suitable coupling means includes a shortened version of a stretch band that includes a hook and loop type fastener system. In practice, the multiple-slotted design may prove to be overly long for comfortable patient use. Accordingly, an alternative embodiment contemplates a single pair of slots and a single belt may be dually used to connect the transducer to the device of the present invention while simultaneously encircling the patient's abdomen. Each of these aforementioned coupling means enables a practitioner to quickly and easily couple the aligning device 10 to a standard transducer 1 of the prior art. For example, FIG. 13 shows the device 10 of the present invention with a central, cylindrical housing 12 having a pair of arms 14 and 16 coupled to a transducer 1 of the prior art. The transducer 1 includes a pair of shoulders 5, each shoulder includes at least one slit 7 that adapts to receive a belt 3 of the prior art or the coupling means of this invention. FIGS. 14 and 15 depict a transducer 1 of the prior art in greater detail, including a portion of the belt 3 and cable 9, which connects the transducer 1 to a fetal monitoring device (not shown).

Located on the top surface 20 of the housing 12 are one or more valve means. In the embodiment of FIGS. 1-3, four recessed valves are shown dispersed along a single radius and equally distant from each other on their circumference. The recessed valve members 22 lie below the top surface 20 so as not to protrude over the surface. The valve members may be positioned flush or below, but it is undesirable to have the valves protrude above the top surface because of comfort for the patient, in this particular embodiment. For example, as FIG. 7 more clearly shows, a recessed valve 22 is disposed on the housing body 12 below a plane perpendicular to a top surface 20 of the housing body. The valve 22 does not protrude above the top surface and disposes below or flush with the top surface.

The housing body 12 encapsulates at least one hollow chamber 24. The chamber includes at least one resiliently deformable wall 26. Silicon bladders, as commonly used in the medical industry, are one possible material well-suited for the wall 26.

Associated with the chamber, a valve means, such as valve 22, provides a means for creating a selectively operable fluid conduit passing through the housing body to the hollow chamber. Accordingly, as a pressurized fluid, such as air, is pumped into the chamber, the resiliently deformable wall 26 expands outside the confines of the housing. For example, FIG. 10 shows a deflated wall 26 and an expanded, or inflated, wall 44. When the device 10 is placed on top of a transducer common in the prior art, the expanding wall 26 exerts a corresponding force on the transducer. When the chamber is offset from the centerline of the housing (and aligned accordingly with the transducer), the transducer is forced downwards and at an angle to the patient. For example, the aligning device 10 includes plurality of hollow chambers wherein the plurality of chambers consists of four chambers.

In the embodiment depicted in FIGS. 1-3, for example, the housing 12 includes four fluid isolated chambers. Each of the four chambers 24 includes at least one corresponding resiliently deformable associated wall 26. Further, each one of the plurality of hollow chambers 24 is in fluid isolation from all of the other chambers. Accordingly, any combination of chambers may be selectively inflated to position the associated transducer in any pitch or rake orientation with respect to the patient. The device 10 is not limited to four chambers, and more or less chambers can be included or diminished as required by application.

Figure 4:
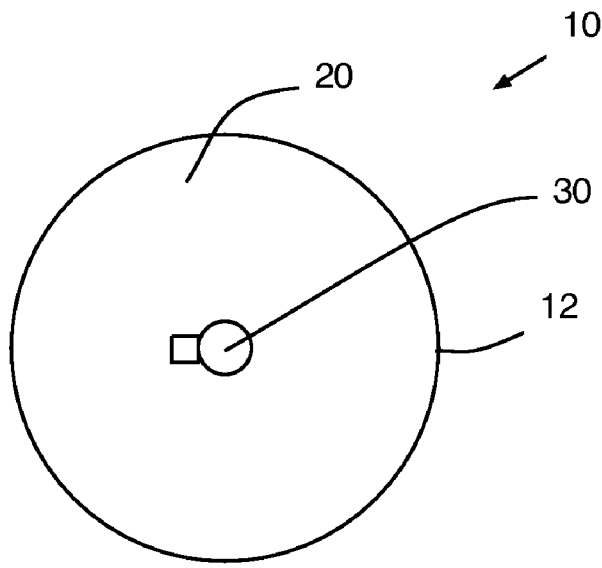
FIG. 4 is a top view of an alternative embodiment of the present invention.
Figure 5:
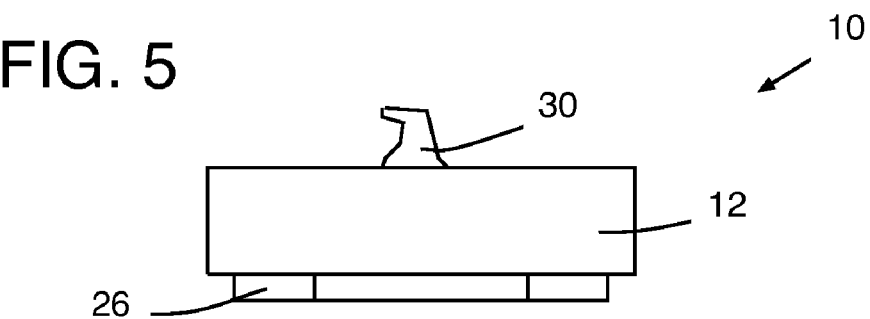
FIG. 5 is a side view of the embodiment of FIG. 4.
Figure 6:
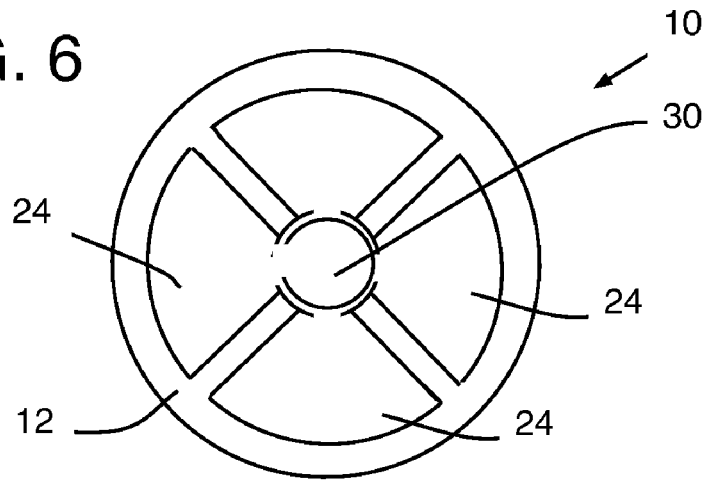
FIG. 6 is a top view with the cover removed of the device of FIG. 4.

In a second embodiment, as FIGS. 4, 5, and 6 show, the device 10 includes a generally flat cylindrical housing 12 having a top surface 20. A centralized protruding nipple valve 30 rotates about an axis and aligns an internal opening with any one of a plurality of corresponding hollow interior chambers 24.

Figure 11:
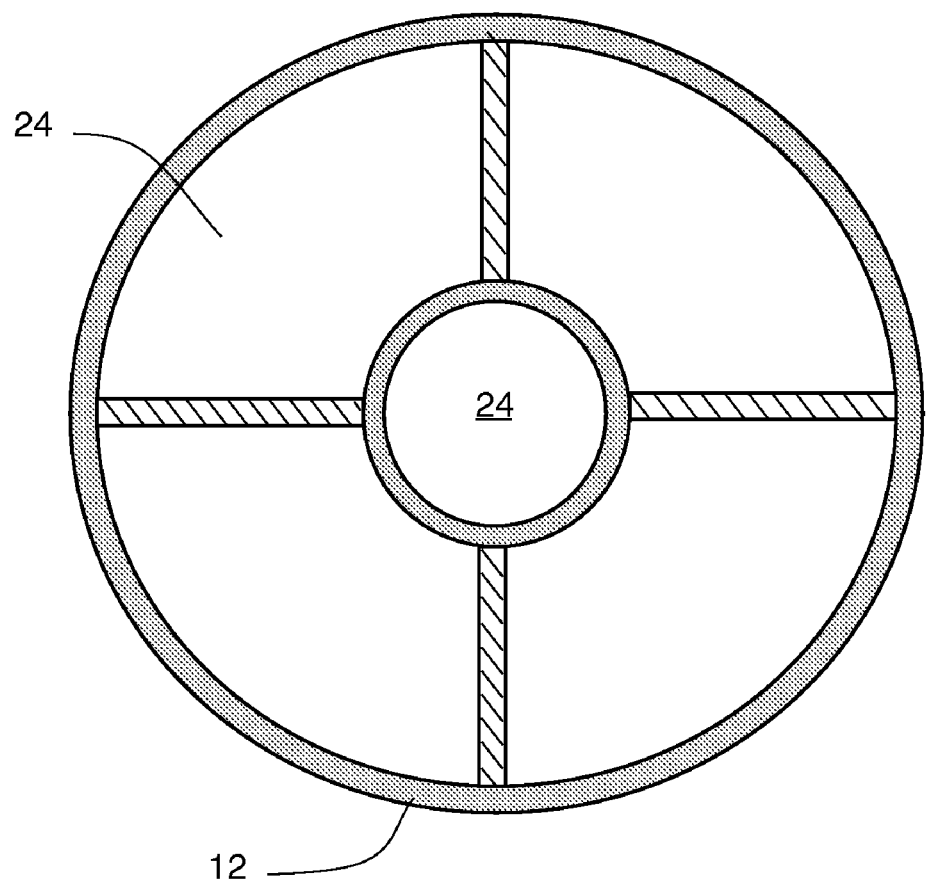
FIG. 11 is a cross-sectional view along the line 11-11 of FIG. 10 and shows the inner chambers of the device according to one embodiment of the present invention.
Figure 12:
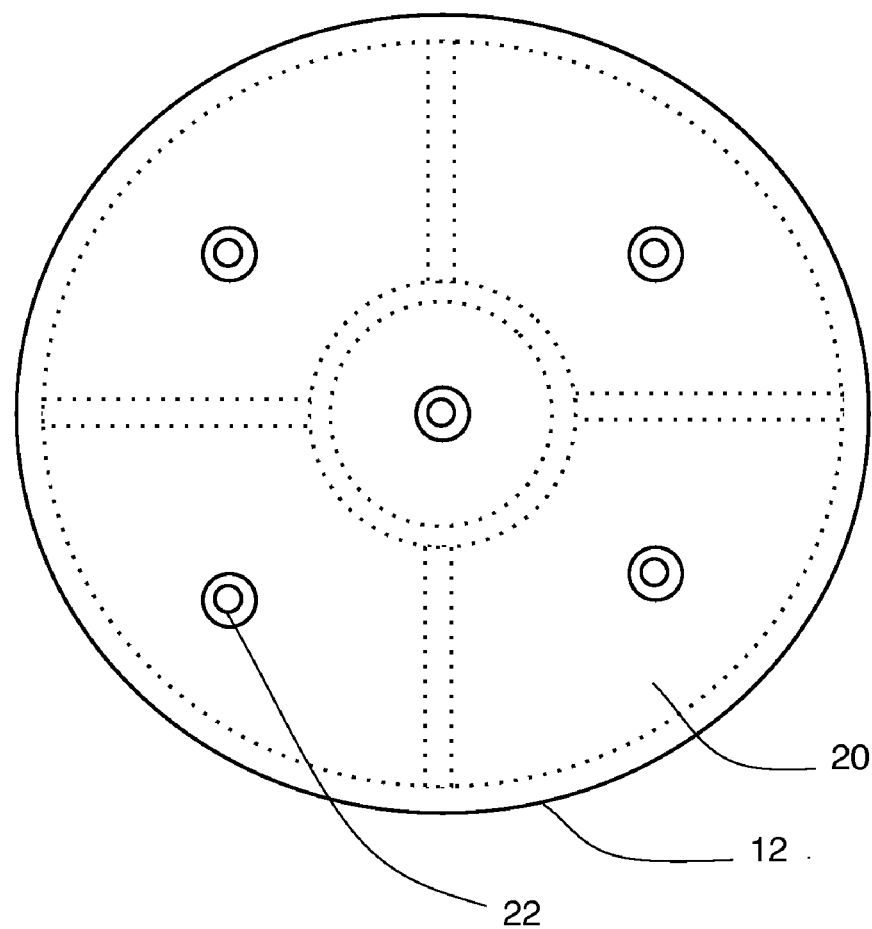
FIG. 12 is a top view of the embodiment of FIG. 11 with the top or cover situated on the housing.

In a third embodiment, as FIGS. 11 and 12 show, the housing body 12 includes five hollow chambers 24. The chambers consist of a first, central chamber, and four radially disposed chambers. Further, each of the five hollow chambers is in fluid isolation from the other hollow chambers. Each chamber has an associated and corresponding resiliently deformable wall 26. Further, this embodiment includes a valve means consisting of five individual valves. Each valve is associated with a specific hollow chamber and enables individual fluid control of its corresponding and associated chamber. Accordingly, each associated resiliently deformable wall 26 may be individually and selectively inflated or deflated by a pumping means coupled via the associated valve.

Figure 7:
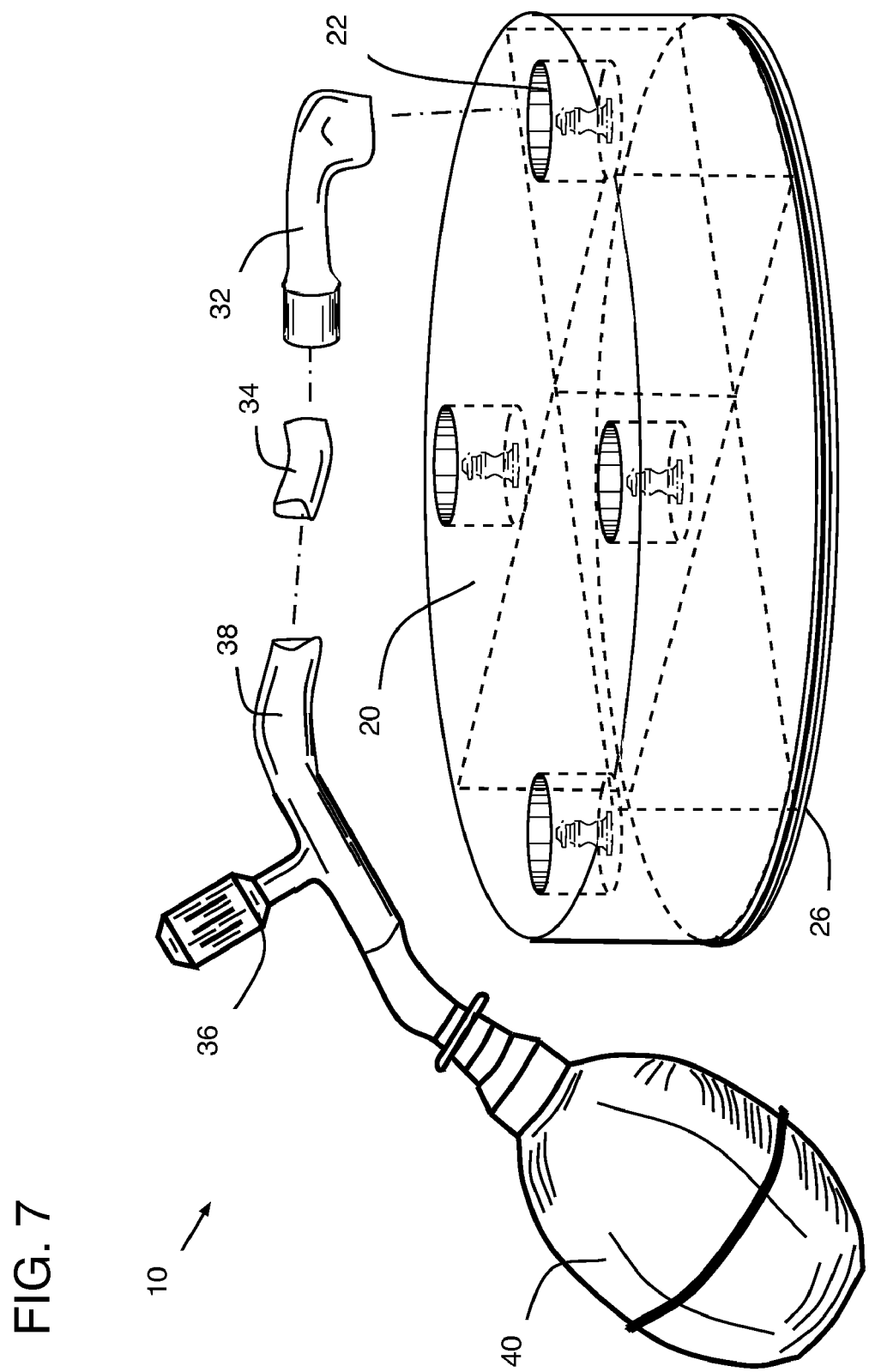
FIG. 7 is a schematic offset view of a device according to one embodiment of the present invention and includes a typical pump apparatus and associated tubing.

In each of the aforementioned embodiments a pumping means is provided to selectively introduce a fluid, such as air, into and out of the various chambers. The pump means selectively coupled to the valve means, the pump means is adapted to selectively inflate or deflate the resiliently deformable wall. For example, as FIG. 7 illustrates, one possible pump means includes a hand-operable bulb pump 40 having a relief valve 36 and tubing 38. Additional hose 34 can be provided to create a desired length. The hose 34 and/or the tubing 38 couples or otherwise connects to a valve-coupling connector 32, which, in turn, adapts to selectively and releaseably couple to the valve means. The pump means adapts to couple to any one of a plurality of valve means. Accordingly, each individual valve means creates a selectively operable fluid conduit passing through the housing body to an associated hollow chamber. Alternatively, the pump means couples to a single valve. The single valve creates a selectively operable fluid conduit to any selected one chamber of the plurality of chambers. As such, the fluid flow path passes through the housing body to the selected chamber.

For example, and by no means exhaustive, U.S. Pat. No. 7,063,676 to Barak et al. on 20 Jun. 2006, U.S. Pat. Nos. 5,931,797, 5,288,286 to Davis et al. on 22 Feb. 1995, and U.S. Pat. No. 2,694,395 to Brown on 16 Nov. 1954 each describe valve means and pumping means contemplated by the present invention.

Figure 9:
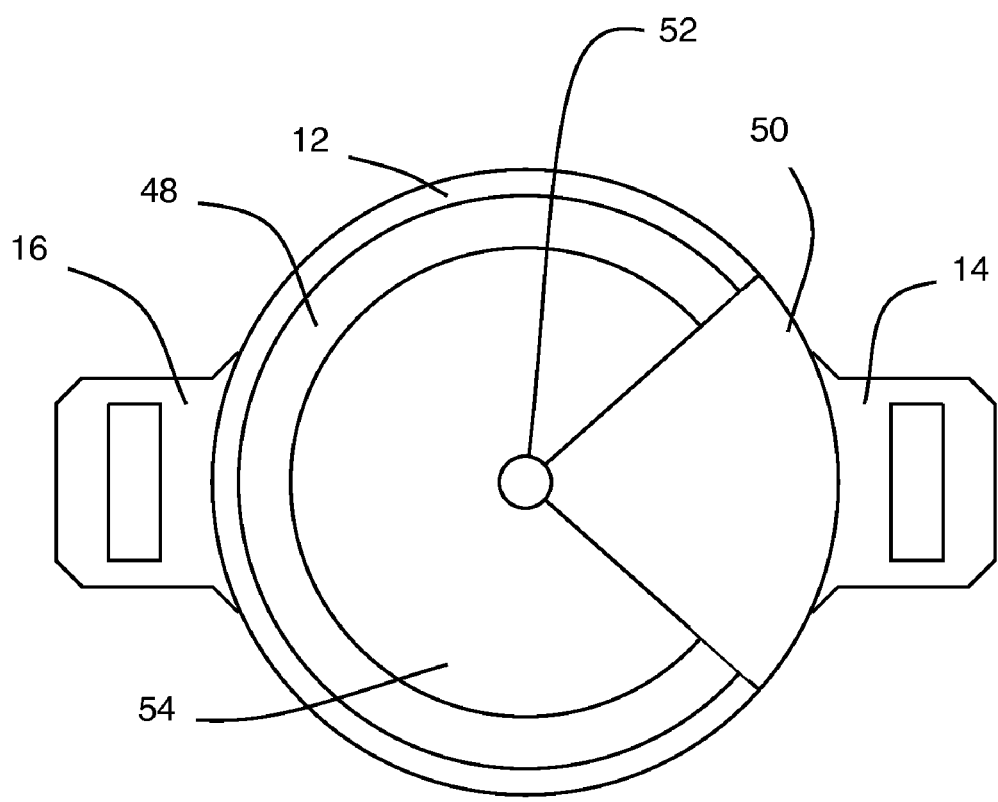
FIG. 9 is a bottom view of an alternative embodiment of the present invention.

FIG. 9 shows another embodiment of the present invention consisting device 10 for positioning a transducer. The device consists of a round, disc-shaped housing 12 having a wedge-shaped protrusion 50 on the underside. This protruding wedge 50 consists of a rigid material and adapts to selectively position by rotating about the pivot-point 52 to any point on the circumference of the housing. Similar to the other described embodiments, the device includes means for coupling to existing, known transducers. The coupling means include a pair of arms 14 and 16 having slots adapted to receive a conventional belt.

The housing 12 includes an outer ring having a concentric slot 48 extending the entire circumference. A solid disk 54 in the center of the housing remains stationary relative to the wedge-shaped protrusion 50, which selectively rotates about a center axis, using the circumferential slot to locate. This wedge, or pie-shaped protrusion extends from a first position that is generally flush with the mean surface defined by the solid disk 54 to a position that lies below the plane defined by this same disk so that the wedge protrusion 50 extends below the housing 12. This enables a practitioner to lift this device, rotate the wedge, and place it in the necessary location so that the wedge angles the transducer at the necessary angle for capturing the FHR. Once properly located, the practitioner simply re-threads the bands through the outer ring to hold it in place. Because the outer ring or slot goes all the way around, the wedge is not limited in where it can be positioned. And, unlike the other embodiments, this particular embodiment does not require an air-bladder to be inflated or deflated.

While the invention has been particularly shown and described with reference to certain embodiments, it will be understood by those skilled in the art that various changes in form and detail may be made without departing from the spirit and scope of the invention.

I claim:

1. An aligning device adapted to be placed on top of a fetal monitoring transducer, the device comprising:
   a housing body encapsulating at least one hollow chamber, the hollow chamber comprising at least one resiliently deformable wall; and
   a valve means for creating a selectively operable fluid conduit passing through the housing body to the hollow chamber, and wherein the housing body comprises: five hollow chambers comprising a first central chamber, and four radially disposed chambers, each of the five hollow chambers being in fluid isolation from the other hollow chambers, each chamber having a corresponding resiliently deformable wall; the valve means further comprises five individual valves, each valve being associated with a specific hollow chamber of the five hollow chambers to enable individual fluid control of each chamber whereby the associated resiliently deformable wall may be selectively inflated or deflated by a pumping means coupled via the associated valve.

2. The aligning device of claim 1 further comprising:
   a pump means selectively coupled to the valve means, the pump means adapted to selectively inflate or deflate the resiliently deformable wall.

3. The aligning device of claim 1 wherein the valve means further comprises:
   said valves being disposed on the housing body and are recessed below a top surface of the housing body whereby the valve does not protrude above the top surface.

4. The aligning device of claim 1 further comprising:
   a pair of arms protruding from the housing body, a first arm disposed opposite from the second arm with the housing body disposed intermediate to the each arm; the first arm comprising a first plurality of slots adapted to receive a coupling means and the second arm comprising a second plurality of slots adapted to receive a second coupling means.

5. The aligning device of claim 2 wherein the pumping means comprises a hand-operable bulb pump having a relief valve and tubing, the tubing including comprising a connector adapted to releaseably couple to the valve means.

6. A fetal monitor-transducer aligning device comprising:
   a housing body encapsulating a plurality of hollow chambers, each chamber comprising at least one corresponding resiliently deformable associated wall and wherein each one of the plurality of hollow chambers is in fluid isolation from all of the other chambers;

a plurality of valve means wherein each individual valve means creates a selectively operable fluid conduit passing through the housing body to the associated hollow chamber; and a pump means selectively coupled to the valve means, the pump means adapted to selectively inflate or deflate the resiliently deformable wall, and wherein the housing body comprises: five hollow chambers comprising a first central chamber, and four radially disposed chambers, each of the five hollow chambers being in fluid isolation from the other hollow chambers, each chamber having a corresponding resiliently deformable wall; and the valve means further comprises five individual valves, each valve being associated with a specific hollow chamber of the five hollow chambers to enable individual fluid control of each chamber whereby the associated resiliently deformable wall may be selectively inflated or deflated by the pumping means coupled via the associated valve.

7. The aligning device of claim 6 wherein each of the plurality of valve means further comprises:

a recessed valve disposed on the housing body below a top surface of the housing body whereby the valve does not protrude above the top surface.

8. The aligning device of claim 6 wherein the housing body comprises:

five hollow chambers comprising a first central chamber, and four radially disposed chambers, each of the five hollow chambers being in fluid isolation from the other hollow chambers, each chamber having a corresponding resiliently deformable wall; and the valve means further comprises five individual valves, each valve being associated with a specific hollow chamber of the five hollow chambers to enable individual fluid control of each chamber whereby the associated resiliently deformable wall may be selectively inflated or deflated by a pumping means coupled via the associated valve.

9. The aligning device of claim 6 further comprising:

at least one arm protruding from the housing body, the arm comprising a plurality of slots adapted to receive a coupling means.

10. The aligning device of claim 6 wherein the pumping means comprises a hand-operable bulb pump having a relief valve and tubing, the tubing including comprising a connector adapted to releaseably couple to the valve means.

11. The aligning device of claim 6 wherein the housing further comprises:

a circumferential slot on an underside portion of the housing adapted to guide a selectively rotatable protruding wedge portion having an inclined surface that extends beyond a bottom plane of the housing body.

* * * * *